(12) United States Patent
Sun et al.

(10) Patent No.: US 12,291,503 B2
(45) Date of Patent: May 6, 2025

(54) CRYSTALLINE FORM OF COMPOUND, METHOD FOR PREPARING THE SAME, PHARMACEUTICAL COMPOSITION AND USE

(71) Applicant: Beijing Konruns Pharmaceutical Co., Ltd., Beijing (CN)

(72) Inventors: Xiaohua Sun, Beijing (CN); Long Wang, Beijing (CN); Hongzhen Yang, Beijing (CN); Huaizhong Hu, Beijing (CN)

(73) Assignee: Beijing Konruns Pharmaceutical Co., Ltd., Beijing (CN)

( * ) Notice: Subject to any disclaimer, the term of this patent is extended or adjusted under 35 U.S.C. 154(b) by 734 days.

(21) Appl. No.: 17/604,745

(22) PCT Filed: Apr. 20, 2020

(86) PCT No.: PCT/CN2020/085695
§ 371 (c)(1),
(2) Date: Oct. 18, 2021

(87) PCT Pub. No.: WO2020/216188
PCT Pub. Date: Oct. 29, 2020

(65) Prior Publication Data
US 2022/0259152 A1  Aug. 18, 2022

(30) Foreign Application Priority Data
Apr. 22, 2019 (CN) .......................... 201910324939.6

(51) Int. Cl.
*C07D 215/22* (2006.01)
*A61P 35/02* (2006.01)
(52) U.S. Cl.
CPC ............ *C07D 215/22* (2013.01); *A61P 35/02* (2018.01); *C07B 2200/13* (2013.01)
(58) Field of Classification Search
CPC .................................................. C07D 215/22
See application file for complete search history.

(56) References Cited

U.S. PATENT DOCUMENTS 10,723,701 B2    7/2020    Zhang et al.

FOREIGN PATENT DOCUMENTS

| CN | 102408411 A | 4/2012 |
|----|-------------|--------|
| CN | 106632253 A | 5/2017 |
| CN | 109384799 A | 2/2019 |
| EP | 3530654 A1  | 8/2019 |
| JP | 2007506777 A | 3/2007 |
| KR | 20190066626 | 6/2019 |
| WO | WO 2005/030140 A2 | 4/2005 |
| WO | WO 2018/196687 A1 | 4/2018 |
| WO | WO 2018/072614 A1 | 8/2019 |

OTHER PUBLICATIONS

International Search Report, dated Jul. 28, 2020, in PCT Application No. PCT/CN2020/085695, 8 pages.
Bavin (1989) "Polymorphism in Process Development," Chemistry and Industry, 527-529.
Carlson et al. (2003) "An integrated high throughput workflow for pre-formulations: Polymorph and salt selection studies," Pharma. Chem., Drug Development, 10-15.
Office Action, dated May 3, 2023 in Canadian Application No. 3,137,209, 4 pp.
Notice of First Review Opinion, dated Apr. 21, 2023 in Chinese Application No. 202080002626, 8 pp.
Byrn et al. (1995) "Pharmaceutical Solids: A Strategic Approach to Regulatory Considerations" Pharmaceutical Research 12(7), pp. 945-954.
Caira, M. (1998) "Crystalline Polymorphism of Organic Compounds" Topics in Current Chemistry 198, pp. 164-208.
Extended European Search Report in European Patent Application 20794784.7, mailed Nov. 30, 2022.
Hirayama, N. (2008) "Handbook for Preparing Crystals of Organic Compounds", pp. 17-65.
Office Action in Japanese Patent Application No. 2021552731, mailed Sep. 27, 2022.
Skrdla et al. (2001) "A Simple Quantitative FT-IR Approach for the Study of a Polymorphic Transformation Under Crystallization Slurry Conditions" Journal of Pharmaceutical and Biomedical Analysis 25(5-6), pp. 731-739.
Takada, N. (2007) "API Form Screening and Selection of Active Drug Ingredients in Drug Discovery Stage" Pharm Stage, 6(10).
Written Opinion in Singapore Patent Application No. 11202111558V, mailed Sep. 15, 2022.
Notice of Allowance, dated Dec. 2, 2024, in Korean Patent Application No. 10-2021-7027707, 10 pp.

*Primary Examiner* — Shawquia Jackson
(74) *Attorney, Agent, or Firm* — Leydig, Voit & Mayer, Ltd.

(57) ABSTRACT

The present disclosure relates to the field of pharmaceutical technology, providing three crystalline forms, i.e., a crystalline form AB, a crystalline form M and a crystalline form F, of the compound 6-[[4-[2-fluoro-4-[[1-[(4-fluorophenyl)aminoformyl]cyclopropanecarbonyl]-amino]phenoxy]-6-methoxy-7-quinolyl]oxy]hexanoic acid for treatment of diseases related to protein kinases AXL and/or VEGFR2. The present disclosure also provides methods for preparing these three crystalline forms and pharmaceutical compositions comprising these three crystalline forms. The crystalline form AB, the crystalline form M and the crystalline form F of the present disclosure all have good chemical stability, and the preparation processes of the three crystalline forms of the present disclosure are simple for implementation with high product yield and purity, allowing stable and mass production that facilitates promotion and application.

15 Claims, 12 Drawing Sheets

CRYSTALLINE FORM OF COMPOUND, METHOD FOR PREPARING THE SAME, PHARMACEUTICAL COMPOSITION AND USE

CROSS-REFERENCE TO RELATED APPLICATIONS

This application is a National Phase of International Application No. PCT/CN2020/085695, filed on Apr. 20, 2020, which claims the priority to Chinese Patent Application No. 201910324939.6 entitled "CRYSTALLINE FORM OF COMPOUND, METHOD FOR PREPARING THE SAME, PHARMACEUTICAL COMPOSITION AND USE" filed before China patent office on Apr. 22, 2019, the entire contents of which are incorporated herein by reference.

TECHNICAL FIELD

The present disclosure relates to the field of pharmaceutical technology, in particular to three crystalline forms of a compound 6-[[4-[2-fluoro-4-[[1-[(4-fluorophenyl) aminoformyl]cyclopropanecarbonyl]amino]phenoxy]-6-methoxy-7-quinolyl]oxy] hexanoic acid, processes for preparation of the crystalline forms, a pharmaceutical composition including the three crystalline forms, and use of the three crystalline forms in treatment of diseases caused by abnormal activity of protein kinases AXL and/or VEGFR2.

BACKGROUND

6-[[4-[2-fluoro-4-[[1-[(4-fluorophenyl)aminoformyl]cyclopropanecarbonyl]amino] phenoxy]-6-methoxy-7-quinolyl]oxy] hexanoic acid is an antitumor drug, which acts primarily on AXL and vascular endothelial growth factor 2 (VEGFR2 or KDR) and is a novel multi-targeted receptor tyrosine kinase inhibitor useful in multiple clinical indications such as acute myeloid leukemia, colon cancer, gastric cancer, lung cancer, thyroid cancer, prostate cancer, hepatocellular carcinoma and kidney cancer. The chemical structure of 6-[[4-[2-fluoro-4-[[1-[(4-fluorophenyl)aminoformyl] cyclopropanecarbonyl]amino] phenoxy]-6-methoxy-7-quinolyl]oxy] hexanoic acid is shown below as a compound 1.

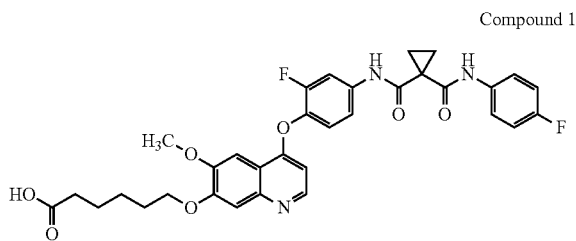 [SMILES: COc1cc2c(Oc3ccc(NC(=O)C4(C(=O)Nc5ccc(F)cc5)CC4)cc3F)ccnc2cc1OCCCCCC(=O)O]

Compound 1

International application WO2018/072614 A1 discloses a compound 1 as an inhibitor of the protein kinases AXL and/or VEGFR2, which can be used to treat diseases (e.g., tumors, etc.) caused by abnormal activity of these two kinases. A process for preparation of the compound 1 can be found in patent application WO 2018/072614 A1.

Good properties related to drug processing, preparation, storage stability and/or usefulness are associated with the crystalline forms of drugs, the study of which is crucial for drug development. Therefore, there is a need to investigate crystalline forms of the compound 1.

SUMMARY

In view of this, the present disclosure provides a crystalline form of a compound 6-[[4-[2-fluoro-4-[[1-[(4-fluorophenyl)aminoformyl]cyclopropanecarbonyl]amino]phenoxy]-6-methoxy-7-quinolyl]oxy] hexanoic acid for use in the treatment of value-added diseases such as cancer.

One aspect of the present disclosure provides three crystalline forms of 6-[[4-[2-fluoro-4-[[1-[(4-fluorophenyl)aminoformyl]cyclopropanecarbonyl]amino]phenoxy]-6-methoxy-7-quinolyl]oxy] hexanoic acid: a crystalline form AB, a crystalline form M, and a crystalline form F.

In the present disclosure, an X-ray powder diffraction pattern of the crystalline form AB represented by an angle of 2θ has diffraction peaks at 4.6±0.1°, 6.7±0.1°, 10.7±0.1°, 16.2±0.1°, 17.0±0.1°, 17.4±0.1°, 19.5±0.1°, 20.7±0.1°, 21.9±0.1°, 22.5±0.1°, 23.8±0.1°, and 25.1±0.1°.

Further, the X-ray powder diffraction pattern of the crystalline form AB represented by an angle of 2θ has diffraction peaks at 4.6±0.1°, 6.7±0.1°, 9.3±0.1°, 9.7±0.1°, 10.7±0.1°, 11.6±0.1°, 13.4±0.1°, 13.8±0.1°, 15.3±0.1°, 16.2±0.1°, 17.0±0.1°, 17.4±0.1°, 18.6±0.1°, 19.5±0.1°, 20.7±0.1°, 21.9±0.1°, 22.3±0.1°, 22.5±0.1°, 23.4±0.1°, 23.8±0.1°, 24.4±0.1°, 25.1±0.1°, 26.0±0.1°, 26.8±0.1°, 27.7±0.1°, 29.7±0.1°, 32.8±0.1°, and 33.1±0.1°.

Further, the X-ray powder diffraction pattern of the crystalline form AB represented by an angle of 2θ is shown in FIG. 3.

Further, TGA and DSC patterns of the crystalline form AB are shown in FIG. 4.

The present disclosure further provides a method for preparing the compound 1 in the crystalline form AB, the method including the steps of:
(1) adding the compound 1 to an alcohol solvent, and heating at a temperature ranging from 75° C. to 80° C. to dissolving the compound 1;
(2) precipitating crystals at a temperature below −5° C., stirring at a temperature ranging from −10° C. to −15° C. to further precipitate crystals; and
(3) filtering and drying the crystals to obtain an off-white solid, i.e., the crystalline form AB.

Preferably, the alcohol solvent is selected from methanol, ethanol, n-propanol, isopropanol, n-butanol, isobutanol, tert-butanol, n-pentanol, tert-pentanol or a mixed solvent containing ethanol; preferably, the mixed solvent containing ethanol is selected from tetrahydrofuran/water/ethanol, tetrahydrofuran/ethanol, or DMF/ethanol.

In the present disclosure, an X-ray powder diffraction pattern of the crystalline form M represented by an angle of 2θ has diffraction peaks at 9.5±0.1°, 10.2±0.1°, 10.6±0.1°, 11.4±0.1°, 13.2±0.1°, 14.3±0.1°, 18.2±0.1°, 18.9±0.1°, 19.3±0.1°, 19.7±0.1°, 20.4±0.1°, 23.3±0.1°, 26.7±0.1°, and 29.6±0.1°.

Further, the X-ray powder diffraction pattern of the crystalline form M represented by an angle of 2θ has diffraction peaks at 9.5±0.1°, 10.2±0.1°, 10.6±0.1°, 11.4±0.1°, 13.2±0.1°, 14.3±0.1°, 15.2±0.1°, 15.7±0.1°, 16.4±0.1°, 17.4±0.1°, 18.2±0.1°, 18.9±0.1°, 19.3±0.1°, 19.7±0.1°, 20.4±0.1°, 22.1±0.1°, 23.3±0.1°, 24.2±0.1°, 25.3±0.1°, 25.7±0.1°, 26.7±0.1°, 27.2±0.1°, 27.7±0.1°, 28.8±0.1°, and 29.6±0.1°.

Further, the X-ray powder diffraction pattern of the crystalline form M represented by an angle of 2θ is shown in FIG. 5.

Further, TGA and DSC patterns of the crystalline form M are shown in FIG. 6.

The present disclosure further provides a method for preparing the crystalline form M of the compound 1, the method including the steps of:
(1) adding the compound 1 to an alcohol solvent and heating at a temperature ranging from 75° C. to 80° C. to dissolve the compound 1;
(2) stirring at a temperature ranging from 10° C. to 30° C. to precipitate crystals; and
(3) filtering and drying the crystals to obtain an off-white solid, i.e., the crystalline form M.

Preferably, the alcohol solvent is selected from methanol, ethanol, n-propanol, isopropanol, n-butanol, isobutanol, tert-butanol, n-pentanol, tert-pentanol or a mixed solvent containing ethanol; preferably, the mixed solvent containing ethanol is selected from tetrahydrofuran/water/ethanol, tetrahydrofuran/ethanol, or DMF/ethanol.

In the present disclosure, an X-ray powder diffraction pattern of the crystalline form F represented by an angle of 2θ has diffraction peaks at 7.1±0.1°, 8.0±0.1°, 10.0±0.1°, 10.9±0.1°, 14.0±0.1°, 15.4±0.1°, 16.0±0.1°, 16.5±0.1°, 17.1±0.1°, 19.5±0.1°, 22.0±0.1°, 25.0±0.1°, and 28.1±0.1°.

Further, the X-ray powder diffraction pattern of the crystalline form F represented by an angle of 2θ has diffraction peaks at 7.1±0.1°, 8.0±0.1°, 9.0±0.1°, 10.0±0.1°, 10.9±0.1°, 11.3±0.1°, 14.0±0.1°, 15.4±0.1°, 16.0±0.1°, 16.5±0.1°, 17.1±0.1°, 18.0±0.1°, 19.5±0.1°, 19.8±0.1°, 20.4±0.1°, 21.4±0.1°, 22.0±0.1°, 22.8±0.1°, 24.4±0.1°, 25.0±0.1°, 26.2±0.1°, 27.7±0.1°, 28.1±0.1°, 29.6±0.1°, and 33.5±0.1°.

Further, the X-ray powder diffraction pattern of the crystalline form F represented by an angle of 2θ is shown in FIG. 7.

Further, TGA and DSC patterns of the crystalline form F are shown in FIG. 8.

The present disclosure further provides a method for preparing the crystalline form F of a compound 1, the method including steps of:
(1) adding the crystalline form AB to dimethylacetamide, dissolving for clarification, and then adding an antisolvent, water, while stirring, and performing stirring to precipitate crystals; and
(2) separating the crystals and performing vacuum drying at a temperature ranging from 22° C. to 30° C. for one day followed by vacuum drying at a temperature ranging from 45° C. to 60° C. for one day.

The present disclosure further provides another method for preparing the crystalline form F of the compound 1, the method including steps of:
(1) adding the compound 1 to an organic solvent and stirring at a temperature ranging from 20° C. to 60° C. to dissolve the compound 1 or to prepare a suspension;
(2) stirring at a temperature ranging from 20° C. to 60° C. with the crystalline form F of the compound 1 as a seed crystal to precipitate crystals; and
(3) filtering and drying the precipitated crystals to obtain an off-white solid, i.e., the crystalline form F, the organic solvent being selected from DMSO, ethyl acetate, methanol, ethanol or a mixed solvent of DMSO/ethyl acetate, or a mixed solvent of DMSO/water.

The present disclosure further provides a method for preparing the crystalline form F of the compound 1, the method including steps of:
(1) adding the crystalline form AB to ethyl acetate, and heating to 50±3° C. to prepare a solid-liquid suspension system; and
(2) stirring and reacting at 50±3 C for 1-2 days with the crystalline form F as a seed crystal to precipitate crystals, filtering the crystals, and drying a filter cake to obtain the crystalline form F.

One aspect of the present disclosure provides a pharmaceutical composition including: at least one of the compound 1 in the crystalline form AB, the compound 1 in the crystalline form M, or the compound 1 in the crystalline form F of the present disclosure; and a pharmaceutically acceptable carrier.

The present disclosure also provides use of the crystalline form AB, the crystalline form M and the crystalline form F of the compound 1 and the pharmaceutical composition comprising these three crystalline forms in the manufacture of a medicament for the treatment of a disease caused by abnormal activity of the protein kinases AXL and/or VEGFR2, such as a tumor or cancer. In particular, the pharmaceutical composition may be useful in the treatment of thyroid cancer (including medullary thyroid cancer), gastric cancer, esophageal cancer, kidney cancer (including renal carcinoma), liver cancer (including hepatocellular carcinoma), ovarian cancer, cervical cancer, cancer of large intestine, cancer of small intestine, brain cancer (including astrocytic tumor, including glioblastoma, giant cell glioblastoma, gliosarcoma, and glioblastoma with oligodendroglia components), leukemia, lung cancer (including non-small cell lung cancer), bone cancer, prostate cancer (including castration-resistant prostate cancer), pancreatic cancer, skin cancer, lymphoma, solid tumor, Hodgkin's disease or non-Hodgkin's lymphoma. Accordingly, the present disclosure also relates to a method for the treatment of the diseases caused by abnormal activity of the protein kinases AXL and/or VEGFR2, and the method of treatment includes administering to a subject the pharmaceutical composition described above.

The pharmaceutical composition described herein may be formulated into a variety of dosage forms including, but not limited to, a variety of oral formulations; preferably, the pharmaceutical composition is a tablet or capsule.

The present disclosure has the following advantageous effects:
1. The crystalline form AB, the crystalline form M and the crystalline form F of the compound 1 of the present disclosure all have good chemical stability with high yield and purity.
2. The methods for preparing the crystalline forms of the present disclosure are simple and easy, allowing stable and batch-wise production, which is advantageous for promotion and application.
3. The crystalline form AB, the crystalline form M and the crystalline form F are stable even under high temperature, high humidity, oxidizing conditions, favoring storage and transportation, and industrial production.
4. The crystalline form AB, the crystalline form M and the crystalline form F of the present disclosure (especially the crystalline form AB) have high bioavailability.

DESCRIPTION OF EMBODIMENTS

Figure 1:
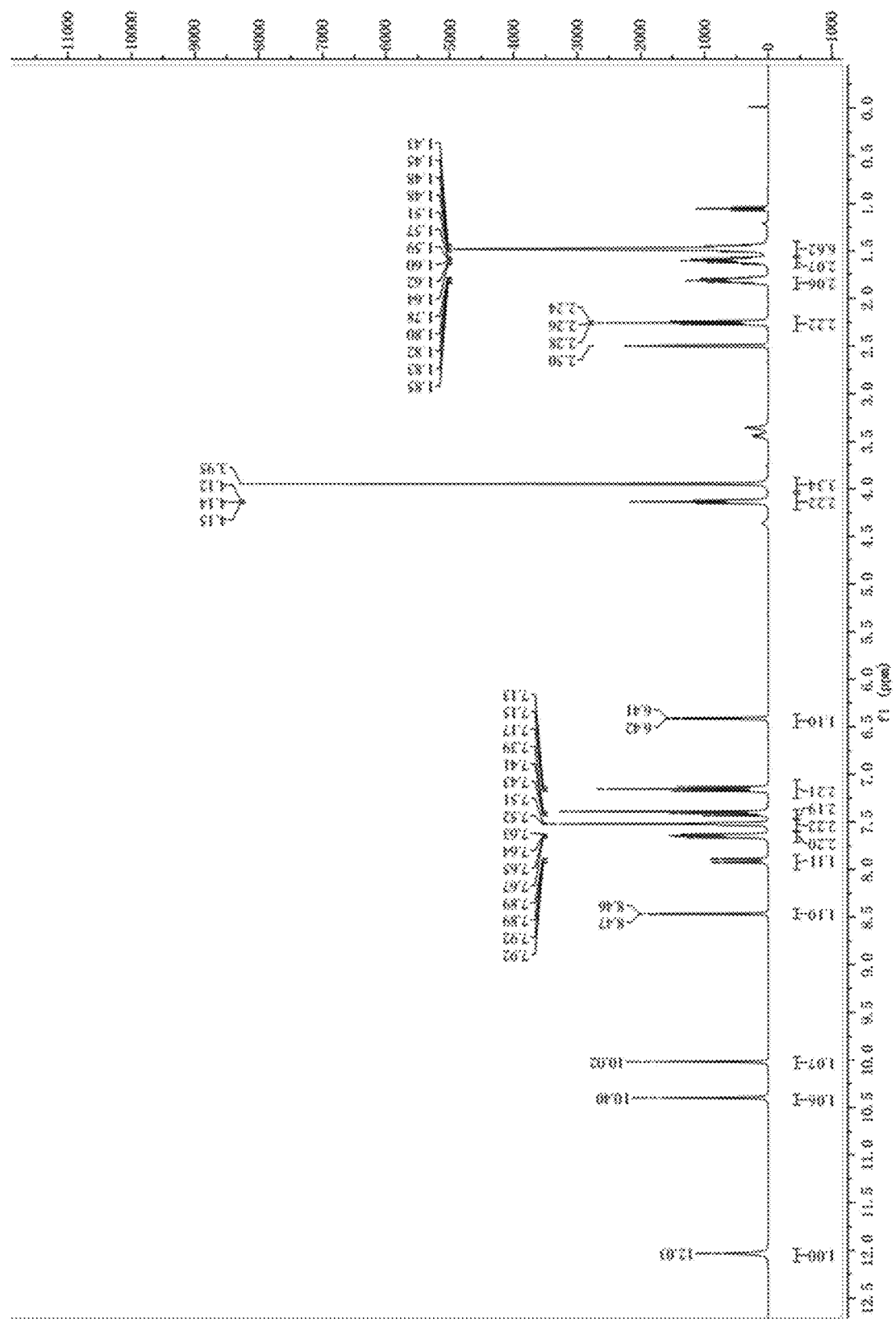
FIG. 1 shows a $^1$H-NMR spectrum of a compound 1 (with deuterated DMSO as a solvent)

The present disclosure will be further illustrated below with reference to examples.

Example 1

For the preparation method of the compound 1, see Example 9 of a compound patent WO 2018/072614 A1. Specifically, the preparation method of the compound 1 is as follows.

NaOH (4.4 g, 110 mmol) was added dropwise to a solution of methyl 6-[[4-[2-fluoro-4-[[1-[(4-fluorophenyl)aminoformyl]cyclopropanecarbonyl]amino]phenoxy]-6-methoxy-7-quinolyl]oxy]caproate (IV-1, 35.0 g, 55.2 mmol, prepared according to the method described in WO2013/040801 A1) in ethanol (350 mL) while stirring; and after completion of the dropwise addition, water (50 mL) was added. The resulting mixture was stirred at 20-25° C. for 18 h, the reaction solution was diluted with water (100 mL), stirred for 20 min, and the pH was adjusted to 3-4 with 1 N HCl. The reaction mixture was concentrated under reduced pressure and approximately 300 mL of ethanol was distilled off. A solid product was collected after filtration to obtain 28.4 g of a crude product which was purified by silica gel column chromatography (an eluent: ethyl acetate:methanol=1:1, v/v) to obtain 6-[[4-[2-fluoro-4-[[1-[(4-fluorophenyl)aminoformyl]cyclopropanecarbonyl]amino]henoxy]-6-methoxy-7-quinolyl]oxy]hexanoic acid (compound 1), 9.6 g (yield: 28.1%).

Analytical data for the compound 1: molecular weight 619.61; the nuclear magnetic hydrogen spectrum is shown in FIG. 1 and the nuclear magnetic hydrogen spectrum data is as follows:

$^1$H-NMR (δ, DMSO-d6,400 MHz): 12.03 (s, 1H, OH), 10.40 (s, 1H, NH), 10.02 (s, 1H, NH), 8.47-8.46 (d, J=4, 1H, CH), 7.89-7.92 (d, J=12, 1H, CH), 7.63-7.67 (d, J=16, 2H, 2CH), 7.51-7.52 (d, J=4, 2H2CH), 7.39-7.43 (t, 2H, 2CH), 7.13-7.17 (t, 2H, 2CH), 6.41-6.42 (d, J=4, 1H, CH), 4.12-4.15 (t, 2H, $CH_2$), 3.95 (s, 3H, $CH_3$), 2.24-2.28 (t, 2H, $CH_2$), 1.78-1.85 (m, 2H, $CH_2$), 1.57-1.64 (m, 2H, $CH_2$), 1.43-1.51 (m, 6H, $3CH_2$).

Figure 2:
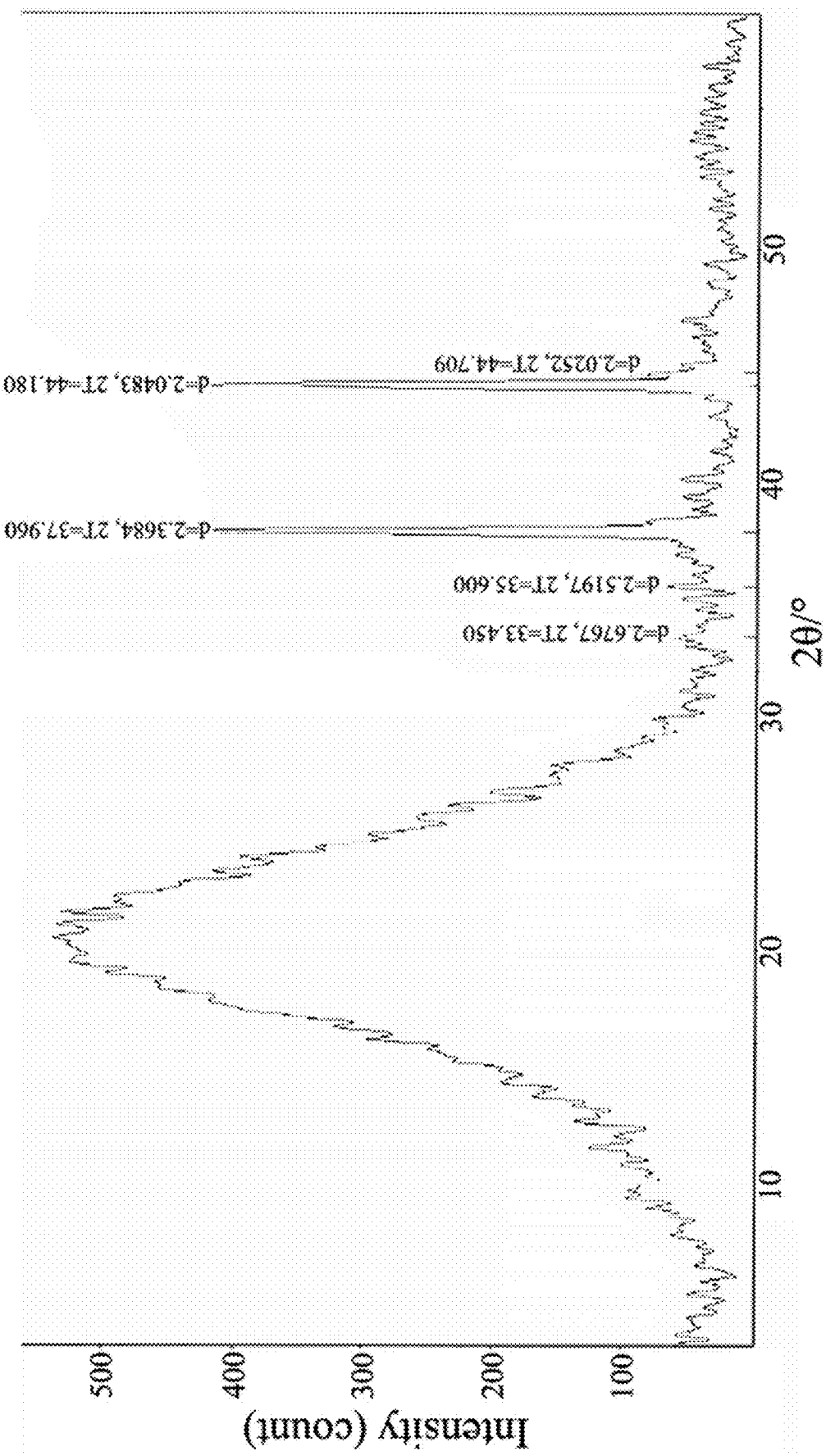
FIG. 2 shows an XRPD pattern of the compound 1 prepared according to a method in the related art.

XRPD test was performed on the solid prepared in this example and the XRPD pattern obtained is shown in FIG. 2.

Example 2

Preparation of the Crystalline Form AB of the Compound 1

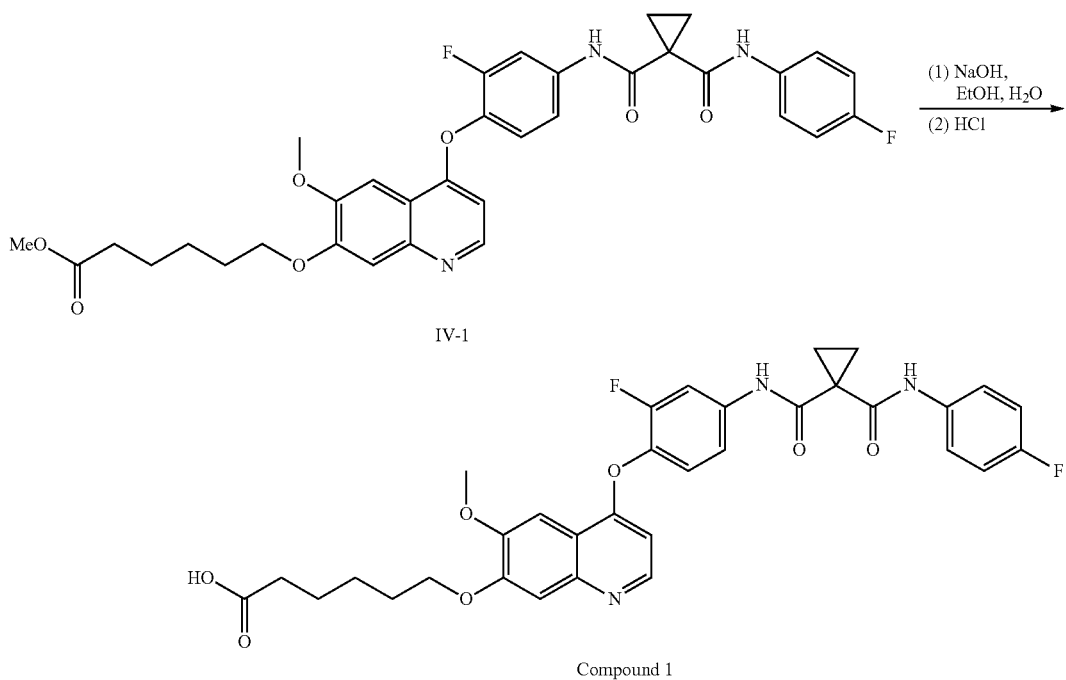

Figure 3:
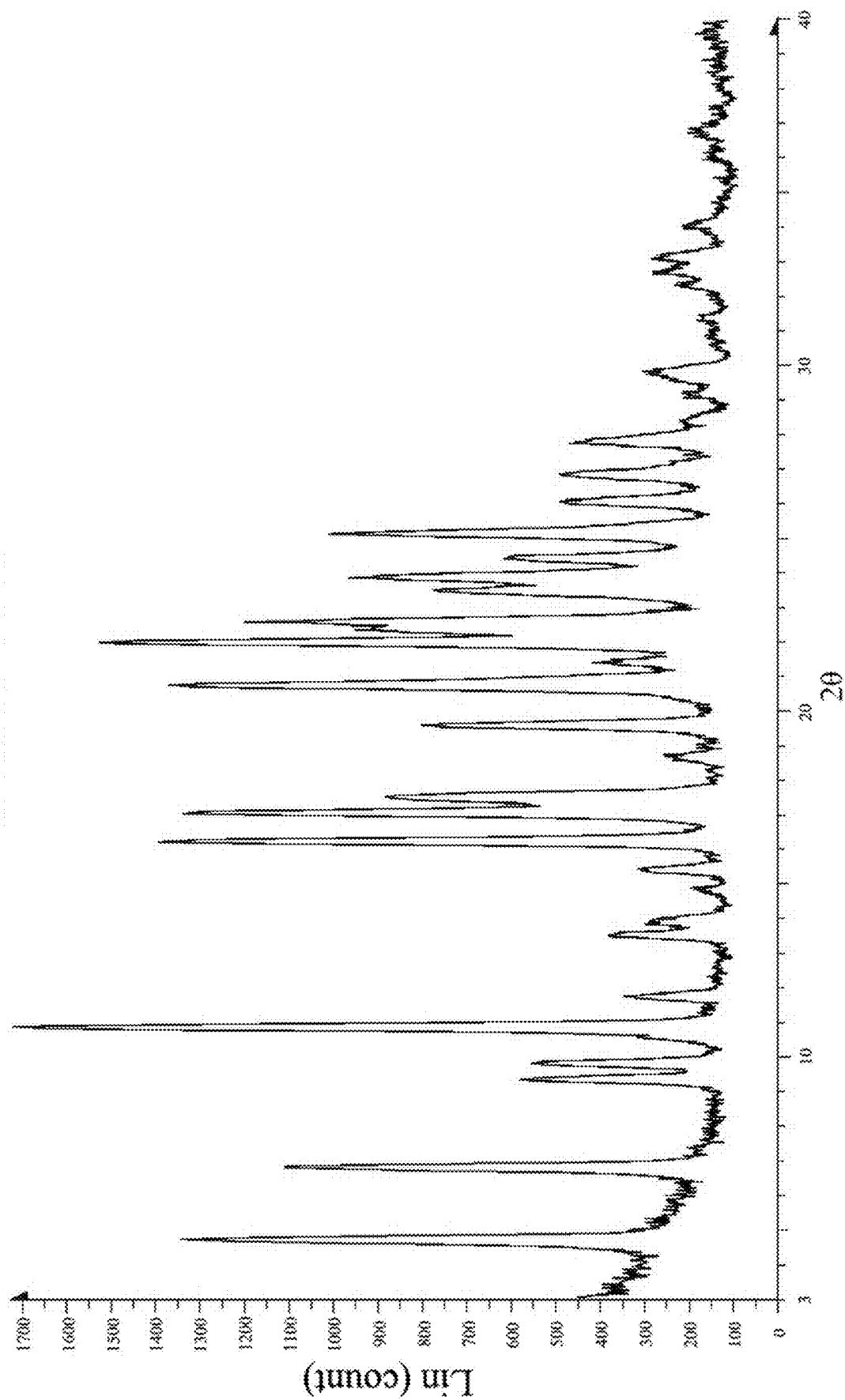
FIG. 3 shows an XRPD pattern of the crystalline form AB of the compound 1.

200.0 g of the compound 1 prepared according to the method of Example 1 was weighed and added into 11 L of absolute ethanol, then stirred mechanically, and heated to 75-80° C. to dissolve the compound 1 for clarification; the solution was cooled to −10° C. to precipitate a solid; after stirring at a temperature of −10±2° C. for 4 h, a large amount of solid was precipitated. Filtration under reduced pressure was performed to obtain a filter cake, which was subjected to vacuum drying at a temperature of 55-60° C. for 10 h to obtain 170.0 g of crystals having an X-ray powder diffraction (XRPD) pattern as shown in FIG. 3, the crystalline form being defined as the crystalline form AB.

Example 3

Preparation of the Crystalline Form AB of the Compound 1

2.0 g of the compound 1 was weighed and added into 12 mL of a mixed solvent of tetrahydrofuran/water (95 v: 5 v); the mixture was heated to reflux until the solid was completely dissolved for clarification, and then the solution was cooled to 40±2° C. to obtain a solution as a solution A. 80 mL ethanol was added to a reaction flask and cooled to −10±2° C.; 0.10 g of the crystalline form AB was then added to the ethanol and stirred to prepare a solid-liquid suspension B. The solution A was added dropwise to the solid-liquid suspension B, with the temperature of the addition process controlled at a temperature ranging from −10° C. to −5° C.; after the dropwise addition was completed, stirring was performed at a temperature ranging from −10° C. to −5° C. to precipitate crystals for about 4 h. Filtration under reduced pressure and drying were carried out to obtain 1.45 g of crystals, the crystalline form of which was the crystalline form AB as detected by XRPD.

Example 4

Preparation of the Crystalline Form M of the Compound 1

Figure 5:
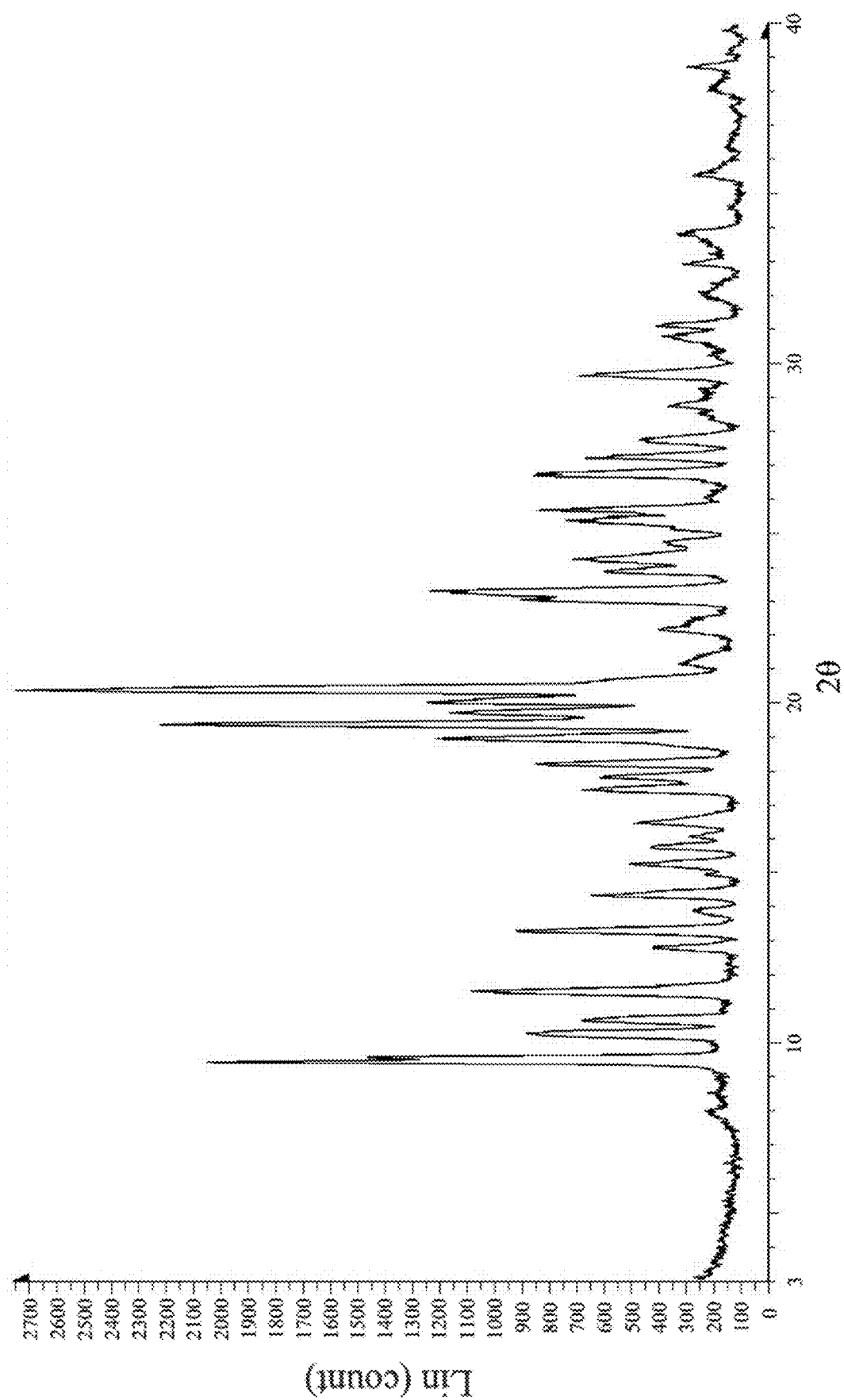
FIG. 5 shows an XRPD pattern of the crystalline form M of the compound 1.

50.0 g of the compound 1 was weighed and added into 2.5 L of absolute ethanol, and the mixture was heated to reflux until the solid was fully dissolved; subsequently, reflux was further continued for 0.5 h. The temperature was naturally decreased to 10-20° C., followed by crystallization with stirring and filtering under reduced pressure; the filter cake was put in a drying cabinet for drying to obtain crystals of the compound 1, the XRPD pattern of which is shown in FIG. 5, the crystalline form being defined as the crystalline form M.

Example 5

Preparation of the Crystalline Form M of the Compound 1

2.0 g of the compound 1 was weighed and added into 100 mL of n-butanol; the mixture was heated and stirred with reflux until the solid was completely dissolved; subsequently, filtering was carried out while the solution was warm; the filtrate was cooled to 20±5° C. to precipitate crystals, followed by filtering under reduced pressure; the filter cake was put in a drying cabinet for drying to obtain crystals of the compound 1, the crystalline form of which is the crystalline form M as detected by XRPD.

Example 6

Preparation of the Crystalline Form M of the Compound 1

2.0 g of the compound 1 was weighed and added into 200 mL of isopropanol; the mixture was heated and stirred with reflux until the solid was completely dissolved; subsequently, filtering was carried out while the solution was warm; the filtrate was naturally cooled to 20±5° C. to precipitate crystals, followed by filtering under reduced pressure; the filter cake was put in a drying cabinet for drying to obtain crystals of the compound 1, the crystalline form of which is the crystalline form M as detected by XRPD.

Example 7

Preparation of the Crystalline Form F of the Compound 1

Figure 7:
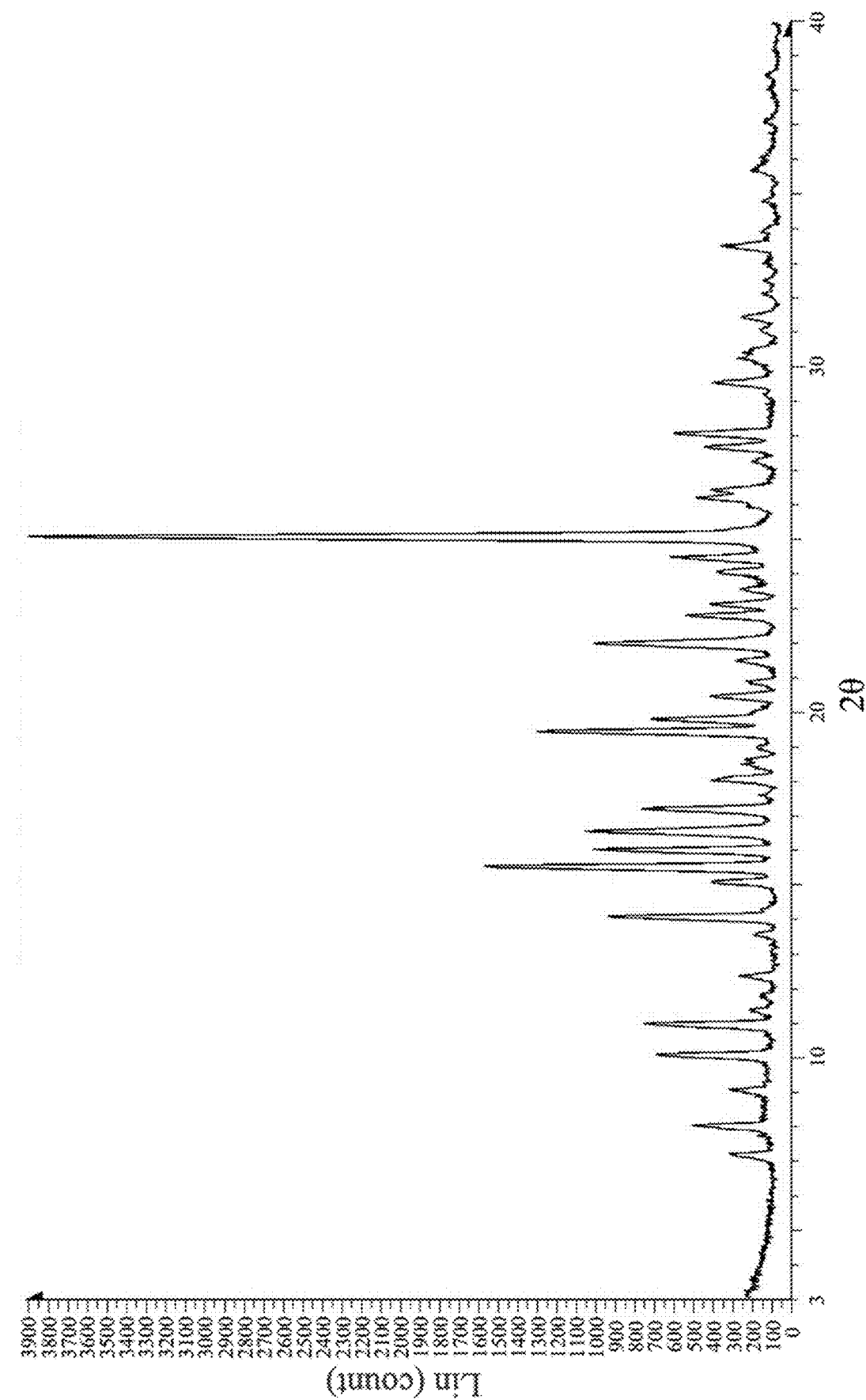
FIG. 7 shows an XRPD pattern of the crystalline form F of the compound 1.

A sample of 200.4 mg of the crystalline form AB was weighed, and added into 1.5 mL of DMAc (Dimethylacetamide) solution to be dissolved; anti-solvent (water) was added dropwise while stirring, with 8 mL water added in total; the solid was isolated by centrifugation (10000 rpm, 2 min), dried under vacuum at room temperature for 1 day and transferred to vacuum drying at 50° C. for 1 day to obtain crystals. The XRPD pattern of the crystals is shown in FIG. 7, the crystalline form being defined as the crystalline form F.

Example 8

(1) 3.27 g of the compound 1 was added to a mixed solution of 2 mL ethyl acetate and 1 mL DMSO (dimethyl sulfoxide); the mixture was stirred at a temperature of 30±3° C. to prepare a solid-liquid suspension;
(2) using the crystalline form F as a seed crystal, stirring was carried out at a temperature of 30±3° C. to precipitate crystals; and
(3) the crystals were filtered and dried to obtain 2.03 g of crystals, the crystalline form of which was the crystalline form F as detected by XRPD.

Example 9

Preparation of the Crystalline Form F of the Compound 1

A mixed solution of 2 mL ethyl acetate and 1 mL dimethyl sulfoxide was prepared, and 2.26 g of the crystalline AB was added to the mixed solution to prepare a saturated solution; a sample of 0.01 g of the crystalline form F was seeded to the saturated solution, magnetically stirred at a temperature of 30±3° C. for 4-5 days, filtered under reduced pressure and dried under vacuum at a temperature of 50±2° C. for 8.5 h to obtain 0.32 g of crystals, the crystalline form of which was the crystalline form F as detected by XRPD.

Example 10

Preparation of the Crystalline Form F of the Compound 1

40 mL of ethyl acetate and 2.00 g of the crystalline AB were added to a reaction flask, and heated to 50±3° C. to prepare a solid-liquid suspension; 0.01 g of the crystalline F was additionally added as a seed crystal to the solid-liquid suspension, stirred to react at a temperature of 50±3° C. for 1-2 days, and then filtered under reduced pressure; the filter cake was dried under vacuum at 50±2° C. at −0.1 MPa for 3 h to obtain crystals, the crystalline form of which was the crystalline form F as detected by XRPD.

Stability Test of Respective Crystal Forms

The stability of the crystalline form AB, the crystalline form M, and the crystalline form F of the compound 1 provided in the present disclosure was examined below (the results were calculated as the weight of the compound 1 for each test group).

Stability Test of the Crystalline Form AB:
Experimental Method:

Accelerated stability test: the compound 1 was contained in vials, and these vials in sealed and open manners respectively were placed in closed containers (desiccators) with a relative humidity of 75%±5%; the desiccators were placed in an incubator at a temperature of 40±2° C. for 7 months; small samples were taken out at 0, 1, 2, 7 months respectively for detection. The test results are shown in FIGS. 9 to 12 and Table 1.

TABLE 1

Results of accelerated stability test

| | Storage Time (Month) | Appearance traits | Purity (HPLC method) | |
|---|---|---|---|---|
| | | | Open | Sealed |
| Experimental group 1 | 0 | This product is off-white to yellowish crystalline powder. | 99.35% | |
| | 1 | This product is off-white to yellowish crystalline powder. | 99.36% | 99.32% |
| | 2 | This product is off-white to yellowish crystalline powder. | 99.35% | 99.34% |
| | 7 | This product is off-white to yellowish crystalline powder. | 99.36% | 99.32% |

The above experimental results show that the crystalline form AB of the compound 1 obtained according to the present disclosure has good stability and high bioavailability, and the appearance traits, particle size, and the like of the obtained crystals are more suitable for pharmaceutical use. The crystalline form AB is easily achieved in terms of scale-up preparation with simple operation, and the resulting crystalline form AB itself is also a thermodynamically stable form. Thus, the crystalline form AB is a more desirable crystal form of the compound in terms of industrial manufacturing processes and quality.

Stability Test of the Crystalline Form M:
Experimental Method:

Accelerated stability test: the crystalline form M of the compound 1 was contained in a petri dish, which was placed in an open manner in a closed container (desiccator) with a relative humidity of 75±5%; the desiccator was placed in an incubator at 40±2° C. for 3 months, and small samples were taken out at 0, 1, 2, 3 months respectively for detection.

TABLE 2

Results of accelerated test

| | Storage Time (Month) | Appearance traits | Purity (HPLC method) | |
|---|---|---|---|---|
| | | | Before grinding | After grinding |
| Experimental group 1 | 0 | This product is off-white to yellowish crystalline powder. | 99.21% | 99.22% |
| | 1 | This product is off-white to yellowish crystalline powder. | 99.36% | 99.37% |
| | 2 | This product is off-white to yellowish crystalline powder. | 99.16% | 99.17% |

TABLE 2-continued

Results of accelerated test

| | Storage Time (Month) | Appearance traits | Purity (HPLC method) | |
|---|---|---|---|---|
| | | | Before grinding | After grinding |
| | 3 | This product is off-white to yellowish crystalline powder. | 99.19% | 99.19% |

The above experimental test data indicates that the crystalline form M before grinding and after grinding had substantially no change in purity in 3 months' accelerated stability test and thus had good stability.

Stability Test of the Form Crystalline F:
Experimental Method:

Accelerated stability test: the crystalline form F of the compound 1 was contained in a petri dish, which was put in an open manner in a closed container (desiccator) with a relative humidity of 75±5%; the desiccator was placed in an incubator at 40±2° C. for 3 months; small samples were taken out at 0, 1, 2 and 3 months respectively for detection.

TABLE 3

Accelerated test results

| | Storage Time (Month) | Appearance traits | Purity (HPLC method) | |
|---|---|---|---|---|
| | | | Before grinding | After grinding |
| Experimental group 1 | 0 | This product is off-white to yellowish crystalline powder. | 99.13% | 99.13% |
| | 1 | This product is off-white to yellowish crystalline powder. | 99.33% | 99.32% |
| | 2 | This product is off-white to yellowish crystalline powder. | 99.09% | 99.07% |
| | 3 | This product is off-white to yellowish crystalline powder. | 99.07% | 99.06% |

The above experimental test data indicate that the crystalline form F before pulverization and after pulverization had substantially no change in purity in 3 months' accelerated stability test and thus had good stability.

Pharmacological Effects of the Crystalline Form AB

Table 4 shows the $IC_{50}$ of the crystalline form AB of the compound 1 against AXL and VEGF-R2.

TABLE 4

| Compound | $IC_{50}$ (M) | |
|---|---|---|
| | AXL | VEGF-R2 |
| Compound 1 (in the crystalline form AB) | 2.4E−10 | 3.8E−10 |
| Sunitinib | 5.4E−07 | 3.2E−09 |

It can be seen from Table 4 that the crystalline form AB of the compound 1 has a lower $IC_{50}$ relative to sunitinib. Thus, the crystalline form AB can serve as a candidate crystalline form for clinical drugs.

Table 5 shows the inhibitory effect of the crystalline form AB of the compound 1 on tumors in different tumor models.

TABLE 5

| Model | KC1036 Dose (crystalline form AB) | Tumor Inhibition Rate % |
|---|---|---|
| Leukemia model MOLM-13 | 1.5 mg/kg | 51.5% |
|  | 6.25 mg/kg | 95.6% |
|  | 3 mg/kg | 81.9% |
|  | 6 mg/kg | 96.7% |
|  | Micronization |  |
| Lung cancer model NCI-H1703 | 50 mg/kg | 99.2% |
|  | 25 mg/kg | 98.5% |
|  | 12.5 mg/kg | 94.7% |
|  | 6.25 mg/kg | 87.0% |

Mice were inoculated subcutaneously with MOLM-13 cells and a human acute myeloid leukemia subcutaneous xenograft tumor model was established. After 14 days of intragastric administration of the crystalline form AB to animals, tumors were taken and tumor volume data were collected. The tumor inhibition rate result for each dose group was presented in the table above. The median effective dose $EC_{50}$ for KC1036 was 1.5 mg/kg; administration of 3 mg/kg significantly inhibited tumor growth; administration of 6 mg/kg or 6.25 mg/kg inhibited tumor growth, and the tumor disappeared in some mice on day 14 after the administration.

NCIH-1703 cells were inoculated subcutaneously in mice to establish a lung cancer subcutaneous xenotransplantation tumor model. After 28 days of intragastric administration of the crystalline form AB to animals, tumors were taken and tumor volume data were collected. The tumor inhibition rate result for each dose group is shown in Table 5 above. The group with KC1036 6.25 mg/kg could significantly inhibit tumor growth, while the group with 12.5 mg/kg could significantly inhibit tumor growth and tumor regression was observed for some mice. The doses of 12.5 mg/kg, 25 mg/kg and 50 mg/kg significantly inhibited tumor growth and the number of tumor regression cases presented a gradual increase.

Bioavailability Analysis of the Crystalline Form AB, the Crystalline Form M, and the Crystalline Form F of the Compound 1

Drug samples of different crystalline forms of the compound 1 were added to a solution of 1 CMC-Na respectively to prepare suspensions, which were administrated to mice by gavage. Drug samples of the different crystalline forms of the compound 1 were prepared into solutions in DMSO/PEG400/water and administered intravenously to mice. After drug administration, blood samples were collected from the dorsal vein of foot at different time points. After anticoagulation with heparin sodium, plasma was extracted by centrifugation. Plasma samples were analyzed by LC-MS/MS to obtain plasma drug concentrations. Pharmacokinetic parameters were calculated by WinNonlin (Phoenix™) The results of the bioavailability analysis for the crystalline form AB, the crystalline form M, and the crystalline form F are presented in Table 6.

TABLE 6

| Crystalline form | | $T_{1/2}$ h | $T_{max}$ h | $C_{max}$ ng/mL | $AUC_{last}$ h*ng/mL | $AUC_{Inf}$ h*ng/mL | AUC_ % Extrap % | MRT h | $AUC_{last}$/D h*mg/mL | F (0→t) (1036 + 1622) % | F (0→∞) (1036 + 1622) % |
|---|---|---|---|---|---|---|---|---|---|---|---|
| M | Mean | 3.61 | 0.917 | 200 | 581 | 1110 | 39 | 5.65 | 58.1 | 13.6 (9.1-18.5) | 14 |
|  | Standard Deviation | 2.11 | 0.585 | 79 | 223 | 694 | 30.2 | 2.88 | 22.3 | 3.6 | 3.6 |
| AB | Mean | 0.86 | 1.33 | 930 | 2399 | 2414 | 1.19 | 1.91 | 240 | 43.1 (26.2-61.8) | 43.2 |
|  | Standard Deviation | 0.11 | 0.75 | 427 | 899 | 881 | 2.3 | 0.37 | 90 | 49.8 | 49.9 |
| F | Mean | 1.7 | 1.5 | 201 | 505 | 675 | 22.7 | 3.05 | 50.5 | 9.6 (5.9-19) | 9.7 |
|  | Standard Deviation | 1.05 | 0.77 | 45 | 82 | 162 | 16.9 | 1.32 | 8.2 | 5.7 | 5.9 |

The results in Table 6 show that the plasma exposure and bioavailability of the crystalline form AB are higher than those of the crystalline M and the crystalline form F. In this regard, the crystalline form AB appears to be more promising for clinical use.

The present disclosure has been disclosed in the preferred embodiments above, which are not intended to limit the claims. Any person skilled in the art could make several possible variations and modifications without departing from the concept of the present disclosure, and therefore the protection scope of the present disclosure shall be set forth by the claims of the present disclosure.

What is claimed is:

1. A crystalline form of compound 1 selected from any one of crystal forms AB, M or F, Compound 1

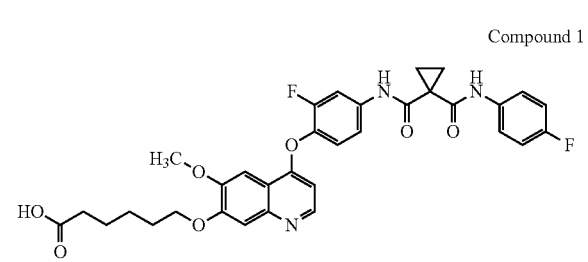 [SMILES: COc1cc2c(Oc3ccc(NC(=O)C4(C(=O)Nc5ccc(F)cc5)CC4)cc3F)ccnc2cc1OCCCCCC(=O)O]

wherein an X-ray powder diffraction pattern of the crystalline form AB represented by an angle of 2θ has diffraction peaks at 4.6±0.1°, 6.7±0.1°, 10.7±0.1°, 16.2±0.1°, 17.0±0.1°, 17.4±0.1°, 19.5±0.1°, 20.7±0.1°, 21.9±0.1°, 22.5±0.1°, 23.8±0.1°, and 25.1±0.1°;

an X-ray powder diffraction pattern of the crystalline form M represented by an angle of 2θ has diffraction peaks at 9.5±0.1°, 10.2±0.1°, 10.6±0.1°, 11.4±0.1°, 13.2±0.1°, 14.3±0.1°, 18.2±0.1°, 18.9±0.1°, 19.3±0.1°, 19.7±0.1°, 20.4±0.1°, 23.3±0.1°, 26.7±0.1°, and 29.6±0.1°; and an X-ray powder diffraction pattern of the crystalline form F represented by an angle of 2θ has diffraction peaks at 7.1±0.1°, 8.0±0.1°, 10.0±0.1°, 10.9±0.1°, 14.0±0.1°, 15.4±0.1°, 16.0±0.1°, 16.5±0.1°, 17.1±0.1°, 19.5±0.1°, 22.0±0.1°, 25.0±0.1°, and 28.1±0.1°.

2. The crystalline form of compound 1 according to claim 1, wherein the X-ray powder diffraction pattern of the crystalline form AB represented by an angle of 2θ has diffraction peaks at 4.6±0.1°, 6.7±0.1°, 9.3±0.1°, 9.7±0.1°, 10.7±0.1°, 11.6±0.1°, 13.4±0.1°, 13.8±0.1°, 15.3±0.1°, 16.2±0.1°, 17.0±0.1°, 17.4±0.1°, 18.6±0.1°, 19.5±0.1°, 20.7±0.1°, 21.9±0.1°, 22.3±0.1°, 22.5±0.1°, 23.4±0.1°, 23.8±0.1°, 24.4±0.1°, 25.1±0.1°, 26.0±0.1°, 26.8±0.1°, 27.7±0.1°, 29.7±0.1°, 32.8±0.1°, and 33.1±0.1°;

the X-ray powder diffraction pattern of the crystalline form M represented by an angle of 2θ has diffraction peaks at 9.5±0.1°, 10.2±0.1°, 10.6±0.1°, 11.4±0.1°, 13.2±0.1°, 14.3±0.1°, 15.2±0.1°, 15.7±0.1°, 16.4±0.1°, 17.4±0.1°, 18.2±0.1°, 18.9±0.1°, 19.3±0.1°, 19.7±0.1°, 20.4±0.1°, 22.1±0.1°, 23.3±0.1°, 24.2±0.1°, 25.3±0.1°, 25.7±0.1°, 26.7±0.1°, 27.2±0.1°, 27.7±0.1°, 28.8±0.1°, and 29.6±0.1°; and the X-ray powder diffraction pattern of the crystalline form F represented by an angle of 2θ has diffraction peaks at 7.1±0.1°, 8.0±0.1°, 9.0±0.1°, 10.0±0.1°, 10.9±0.1°, 11.3±0.1°, 14.0±0.1°, 15.4±0.1°, 16.0±0.1°, 16.5±0.1°, 17.1±0.1°, 18.0±0.1°, 19.5±0.1°, 19.8±0.1°, 20.4±0.1°, 21.4±0.1°, 22.0±0.1°, 22.8±0.1°, 24.4±0.1°, 25.0±0.1°, 26.2±0.1°, 27.7±0.1°, 28.1±0.1°, 29.6±0.1°, and 33.5±0.1°.

3. The crystalline form of compound 1 according to claim 1, wherein the X-ray powder diffraction pattern of the crystalline form AB represented by an angle of 2θ is shown in FIG. 3;

the X-ray powder diffraction pattern of the crystalline form M represented by an angle of 2θ is shown in FIG. 5; and the X-ray powder diffraction pattern of the crystalline form F represented by an angle of 2θ is shown in FIG. 7.

Figure 4:
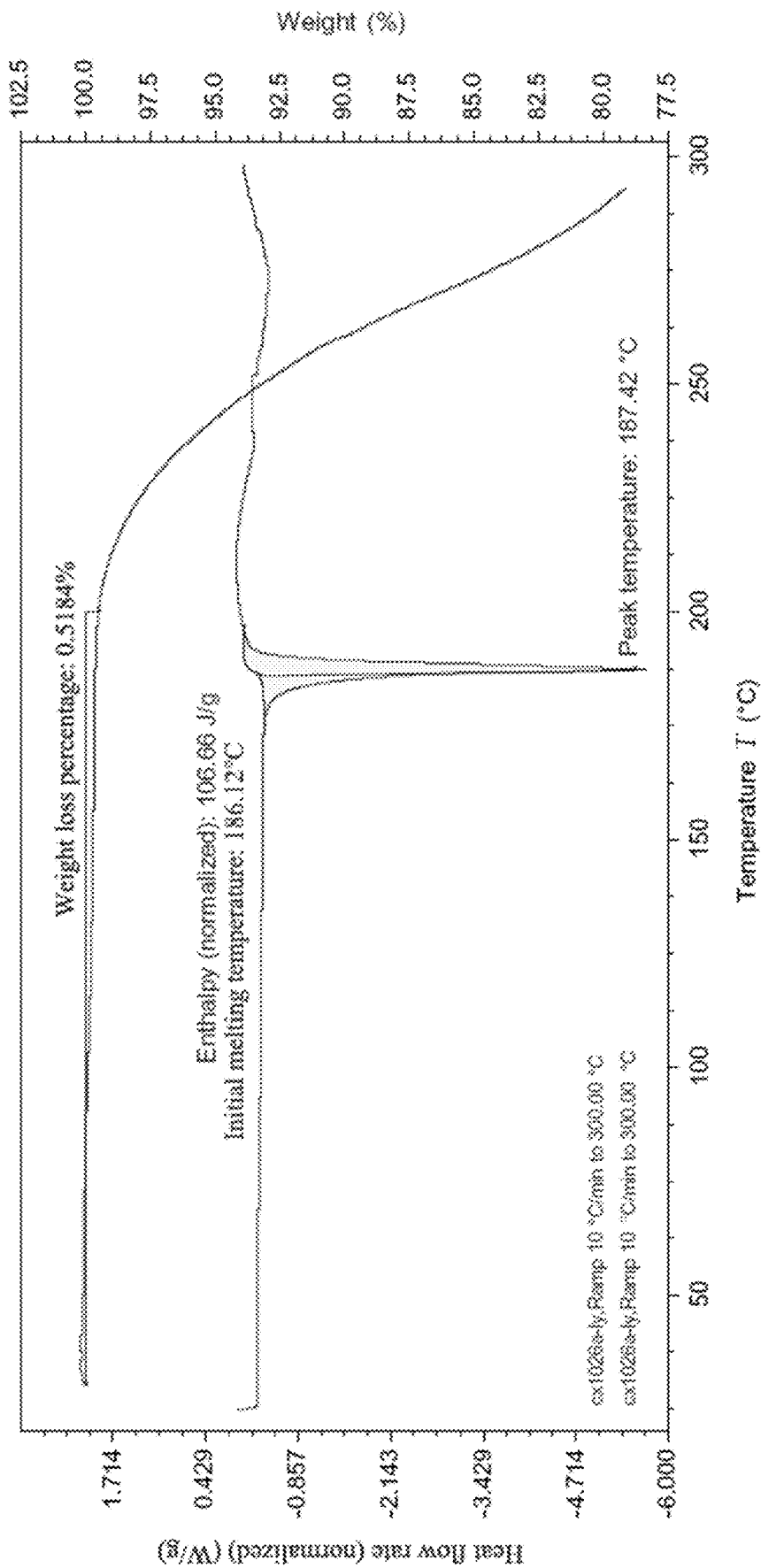
FIG. 4 shows TGA and DSC patterns of the crystalline form AB of the compound 1.
Figure 6:
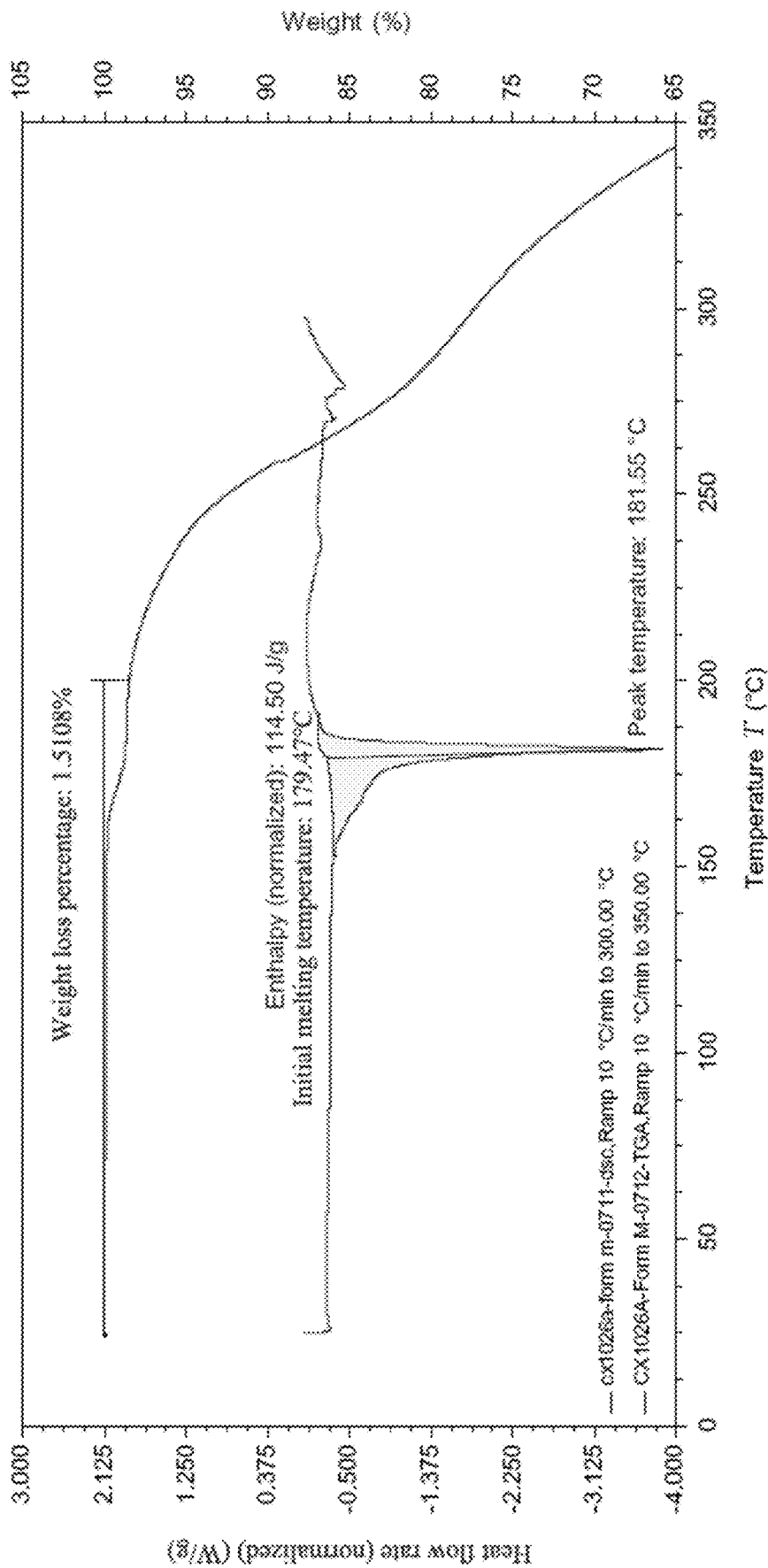
FIG. 6 shows TGA and DSC patterns of the crystalline form M of the compound 1.

4. The crystalline form of compound 1 according to claim 1, wherein TGA and DSC patterns of the crystalline form AB are shown in FIG. 4;

TGA and DSC patterns of the crystalline form M are shown in FIG. 6; and

Figure 8:
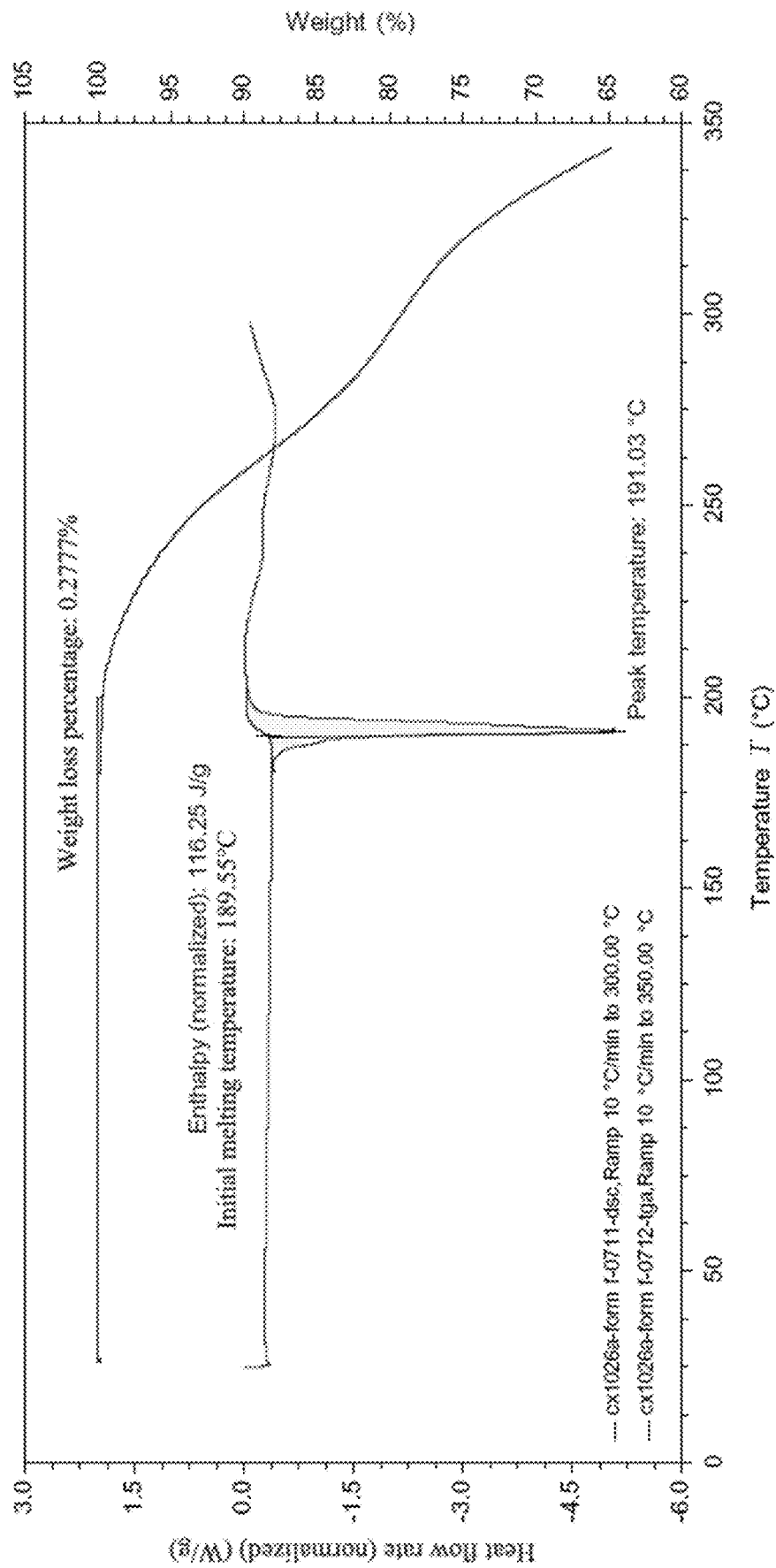
FIG. 8 shows TGA and DSC patterns of crystalline form F of the compound 1.
Figure 9:
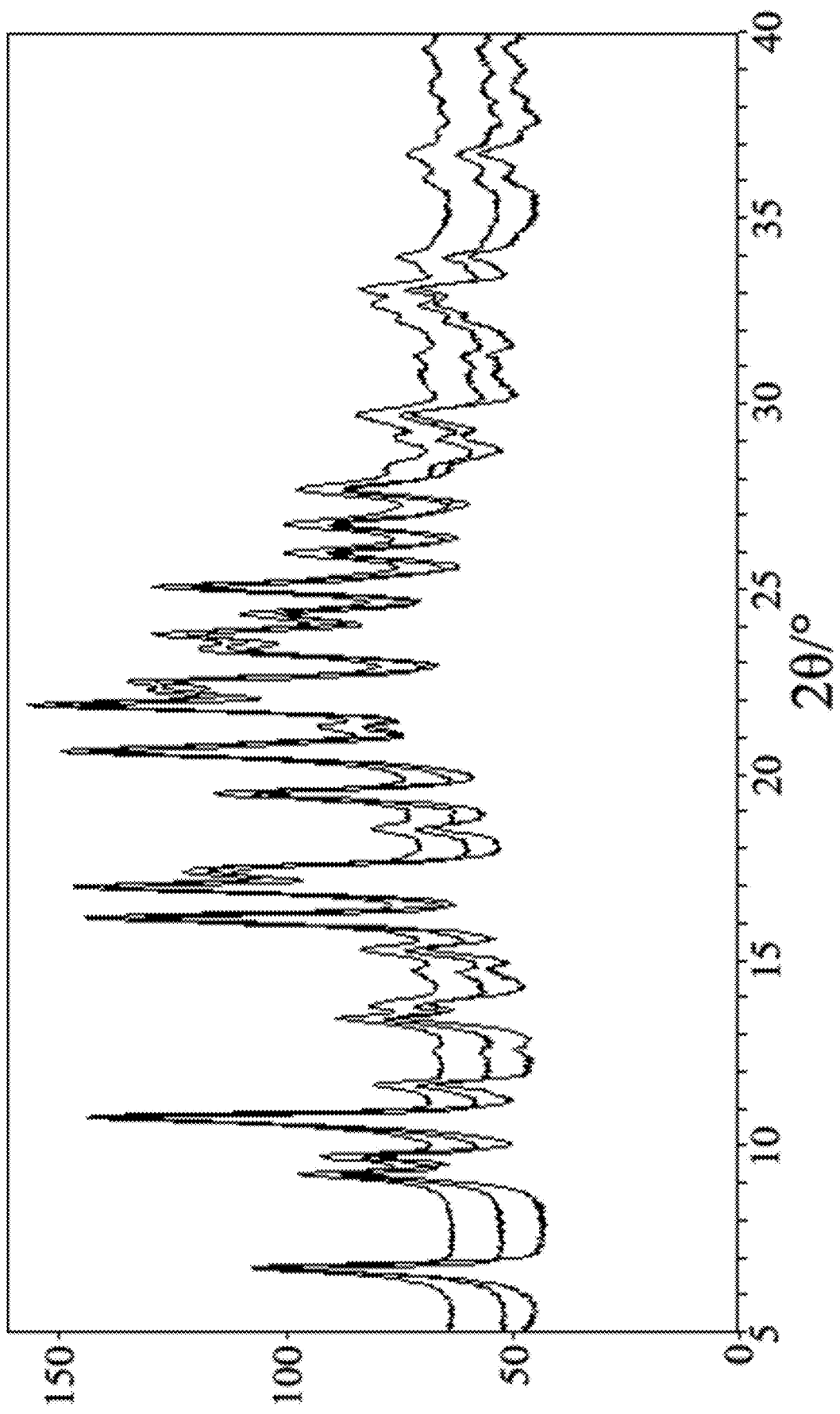
FIG. 9 shows XRPD overlay of the crystalline form AB of the compound 1 prior to accelerated stability test versus at the time of one month after the accelerated stability test (0 month, one month sealed, one month open from top to bottom in order)
Figure 10:
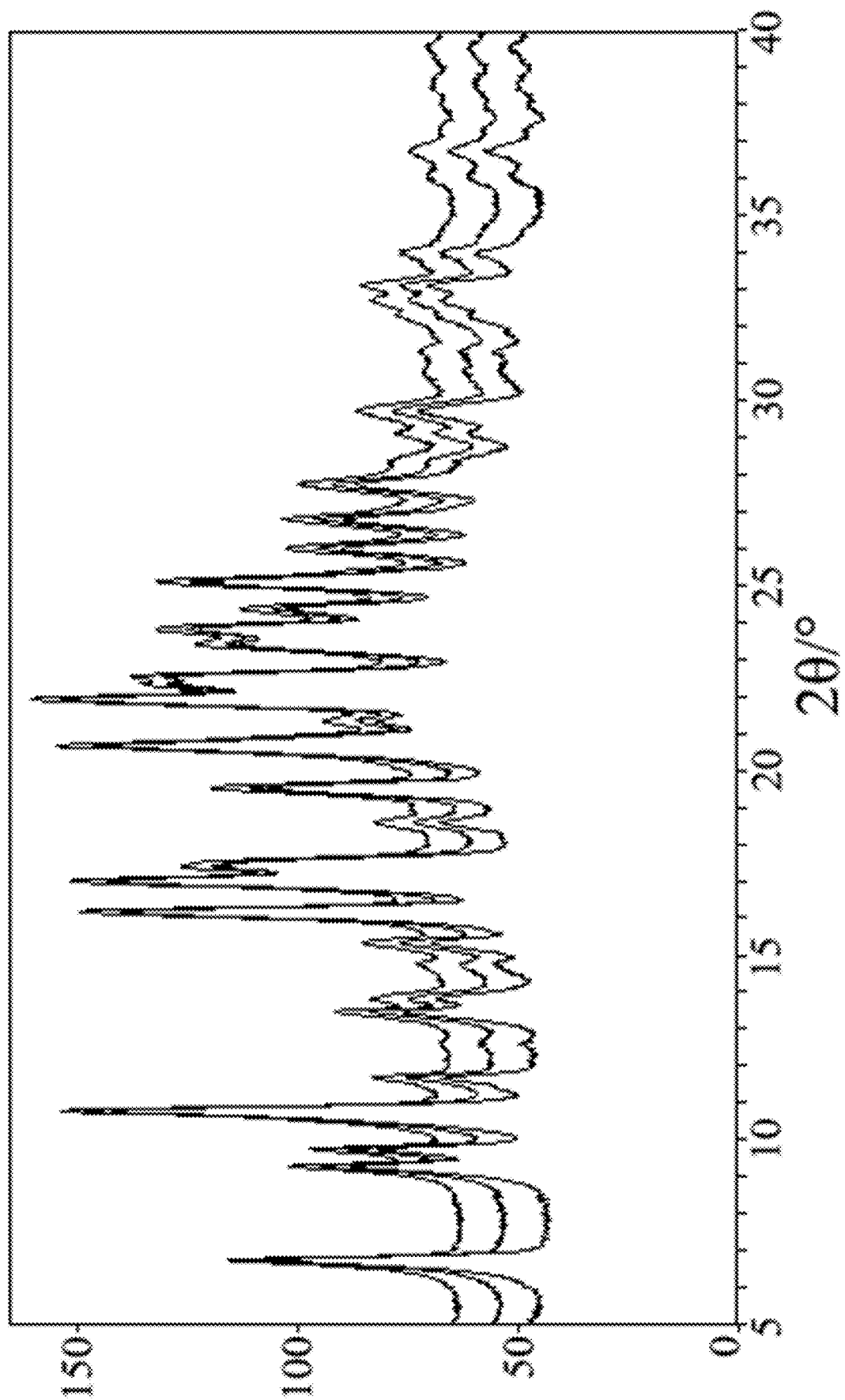
FIG. 10 shows XRPD overlay of the crystalline form AB of the compound 1 prior to accelerated stability test versus at the time of seven months after the accelerated stability test (0 month, one month sealed, one month open from top to bottom in order)
Figure 11:
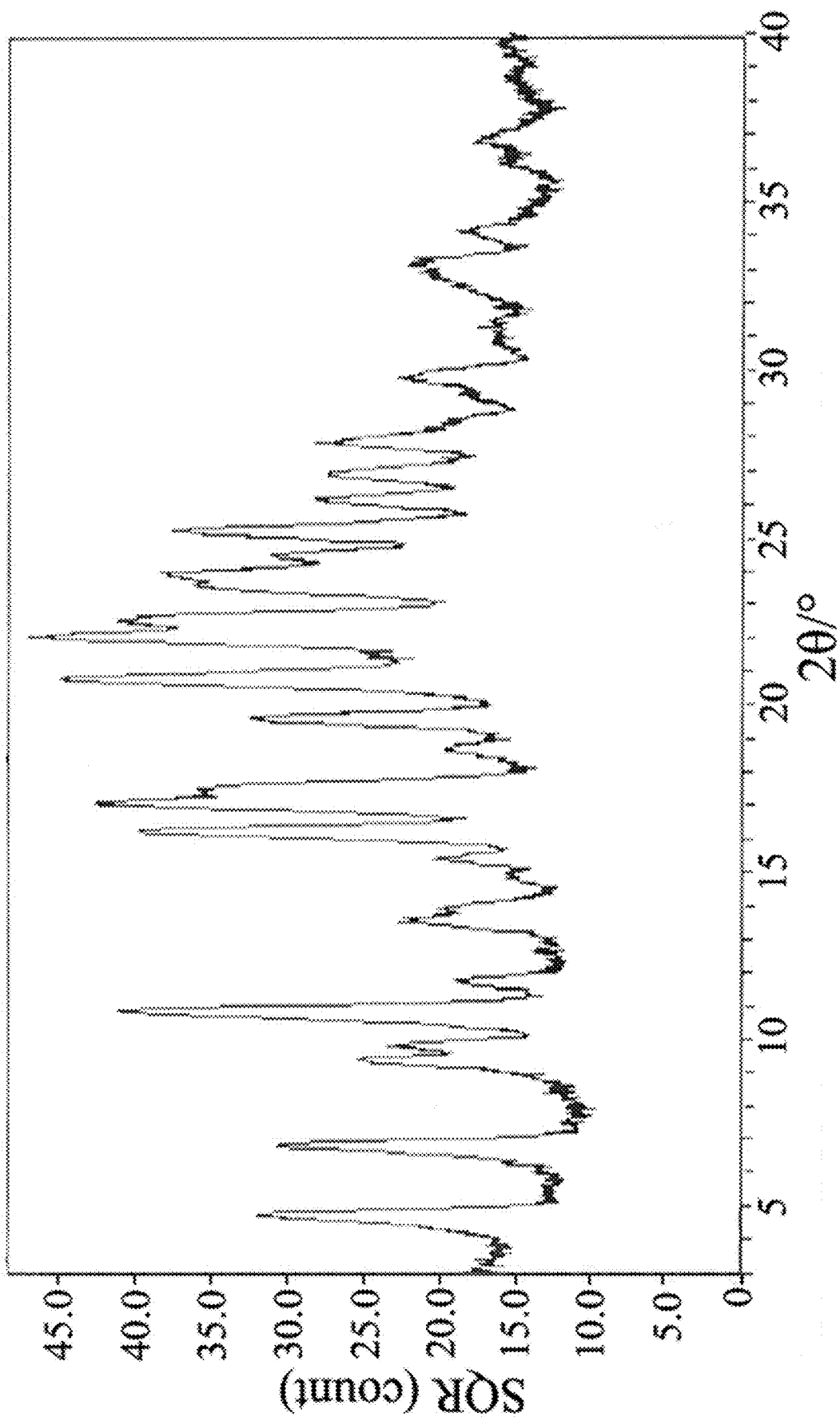
FIG. 11 illustrates an XRPD pattern of the crystalline form AB of the compound 1 at the time of seven months after accelerated stability test (small angle-sealed)
Figure 12:
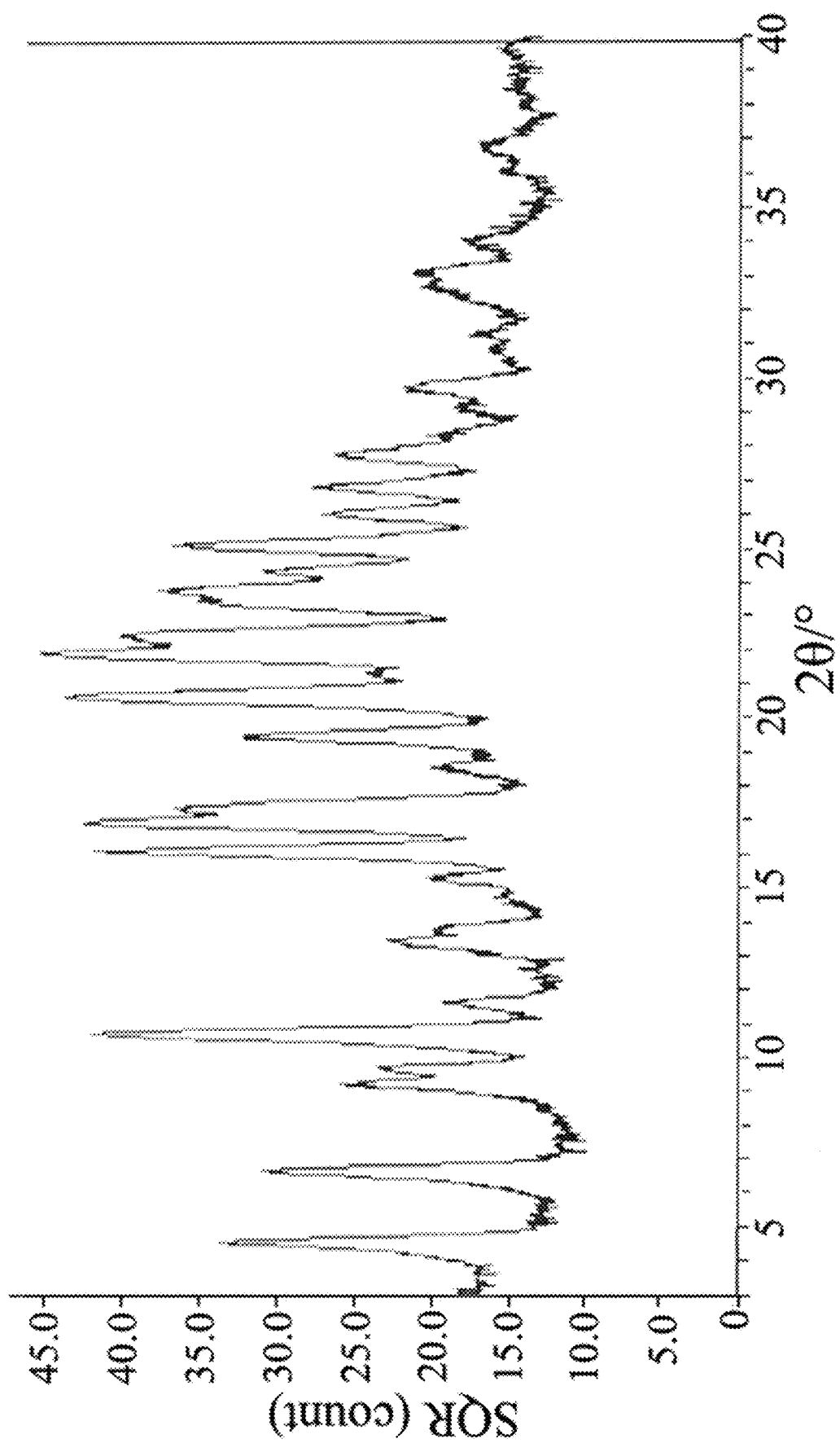
FIG. 12 shows an XRPD pattern (small angle-open) of the crystalline form AB of the compound 1 at the time of seven months after accelerated stability test.

TGA and DSC patterns of the crystalline form F are shown in FIG. 8.

5. A method for preparing the crystalline form of compound 1 according to claim 1, wherein the method for preparing the crystalline form AB comprises:

adding the compound 1 to an alcohol solvent, heating at a temperature ranging from 75° C. to 80° C. to dissolve the compound 1;

precipitating crystals at a temperature below −5° C., and stirring at a temperature ranging from −10° C. to −15° C. to further precipitate crystals; and filtering and drying the crystals to obtain the crystalline form AB, wherein the method for preparing the crystalline form M comprises:

adding the compound 1 to an alcohol solvent and heating to dissolve the compound 1;

stirring at a temperature ranging from 10° C. to 30° C. to precipitate crystals; and filtering and drying the crystals to obtain the crystalline form M, wherein the method for preparing the crystalline form F is selected from any one of Methods I, II or III, wherein the Method I comprises:

adding the crystalline form AB to dimethylacetamide, dissolving for clarification, adding an anti-solvent of water while stirring, and performing stirring to precipitate crystals; and separating the crystals and performing vacuum drying at a temperature ranging from 22° C. to 30° C. followed by vacuum drying at a temperature ranging from 45° C. to 60° C., to obtain the crystalline form F, wherein the Method II comprises:

adding the compound 1 to an organic solvent and stirring at a temperature ranging from 20° C. to 60° C. to dissolve the compound 1 or to prepare a suspension;

stirring at a temperature ranging from 20° C. to 60° C. with the crystalline form F as a seed crystal to precipitate crystals; and filtering and drying the crystals to obtain the crystalline form F, wherein the Method III comprises:

adding the crystalline form AB to ethyl acetate, and heating to 50±3° C. to prepare a solid-liquid suspension system; and stirring and reacting at 50±3° C. for 1-2 days with the crystalline form F as a seed crystal to precipitate crystals, filtering the crystals, and drying a filter cake to obtain the crystalline form F.

6. The method according to claim 5, wherein the alcohol solvent in the method for preparing the crystalline form AB is selected from methanol, ethanol, n-propanol, isopropanol, n-butanol, isobutanol, tert-butanol, n-pentanol, tert-pentanol or a mixed solvent containing ethanol.

7. The method according to claim 6, wherein the mixed solvent containing ethanol is selected from tetrahydrofuran/water/ethanol, tetrahydrofuran/ethanol, or DMF/ethanol.

8. The method according to claim 5, wherein the alcohol solvent in the method for preparing the crystalline form M is selected from methanol, ethanol, n-propanol, isopropanol, n-butanol, isobutanol, tert-butanol, n-pentanol, tert-pentanol or a mixed solvent containing ethanol.

9. The method according to claim 8, wherein the mixed solvent containing ethanol is selected from tetrahydrofuran/water/ethanol, tetrahydrofuran/ethanol, or DMF/ethanol.

10. The method according to claim 5, wherein the organic solvent in the Method II is selected from DMSO, ethyl acetate, methanol, ethanol or a mixed solvent of DMSO/ethyl acetate, or a mixed solvent of DMSO/water.

11. A pharmaceutical composition, comprising: at least one of the compound 1 in the crystalline form AB, M or F according to claim 1; and a pharmaceutically acceptable carrier.

12. A pharmaceutical composition according to claim 11, wherein the pharmaceutical composition is a tablet or a capsule.

13. A method for treatment of a disease caused by abnormal activity of protein kinases AXL and/or VEGFR2, comprising:

administering the compound 1 in the crystalline form AB, M or F according to claim 1 to a subject in need of treatment thereof.

14. The method according to claim 13, wherein the disease caused by abnormal activity of protein kinases AXL and/or VEGFR2 is selected from thyroid cancer, gastric cancer, esophageal cancer, kidney cancer, liver cancer, ovarian cancer, cervical cancer, cancer of large intestine, cancer of small intestine, brain cancer, leukemia, lung cancer, bone cancer, prostate cancer, pancreatic cancer, skin cancer, lymphoma, solid tumor, Hodgkin's disease, and non-Hodgkin's lymphoma.

15. The method according to claim 14, wherein the thyroid cancer is medullary thyroid cancer;
- the kidney cancer is renal carcinoma;
- the liver cancer is hepatocellular carcinoma;
- the brain cancer is astrocytic tumor, wherein the astrocytic tumor is selected from glioblastoma, giant cell glioblastoma, gliosarcoma, and glioblastoma with oligodendroglia components;
- the lung cancer is non-small cell lung cancer; and
- the prostate cancer is castration-resistant prostate cancer.

* * * * *